US00PP28173P3

(12) United States Plant Patent

Swartz et al.

(10) Patent No.: US PP28,173 P3
(45) Date of Patent: Jul. 11, 2017

(54) RASPBERRY PLANT NAMED 'PEARL'

(50) Latin Name: ***Rubus idaeus* L.**
Varietal Denomination: Pearl

(71) Applicant: FIVE ACES BREEDING LLC, Oakland, MD (US)

(72) Inventors: Harry Jan Swartz, Oakland, MD (US); Eva McCarthy, Faversham (GB); Peter Edward Vinson, Faversham (GB)

(73) Assignee: Five Aces Breeding LLC, Oakland, MD (US)

( * ) Notice: Subject to any disclaimer, the term of this patent is extended or adjusted under 35 U.S.C. 154(b) by 24 days.

(21) Appl. No.: 14/756,627

(22) Filed: Sep. 28, 2015

(65) Prior Publication Data

US 2016/0128254 P1 May 5, 2016

(30) Foreign Application Priority Data

Nov. 4, 2014 (QZ) ..... PBR 2014/2771

(51) Int. Cl.
*A01H 5/08* (2006.01)

(52) U.S. Cl.
USPC ..... Plt./204

(58) Field of Classification Search
USPC ..... Plt./204
See application file for complete search history.

(56) References Cited

U.S. PATENT DOCUMENTS

| | | | |
|---|---|---|---|
| PP10,412 | P | 5/1998 | Swartz et al. |
| PP10,610 | P | 9/1998 | Swartz et al. |
| PP11,418 | P | 6/2000 | McNicol et al. |
| PP12,173 | P2 | 10/2001 | Swartz et al. |
| PP12,350 | P2 | 1/2002 | Swartz et al. |
| PP14,804 | P2 | 5/2004 | Fear et al. |
| PP18,246 | P3 | 11/2007 | Moore |
| PP19,430 | P3 | 11/2008 | Swartz |
| PP20,773 | P3 | 2/2010 | Hall et al. |
| PP21,007 | P3 | 5/2010 | Swartz |
| PP21,185 | P3 | 8/2010 | Hall et al. |
| PP22,731 | P2 | 5/2012 | Fear et al. |
| PP23,375 | P3 | 2/2013 | Weber |
| PP23,477 | P3 | 3/2013 | Hamilton et al. |

OTHER PUBLICATIONS

Upov Pluto Plant Variety Database Dec. 8, 2016 (retrieved from the Internet at <https://www3.wipo.int/pluto/user/en/index.jsp> one page.*

Upov Pluto Plant Variety Database Mar. 16, 2017, retrieved on Mar. 16, 2017, retrieved from the Internet at <http://www.upov.int/pluto/en/index.jsp> 6 total pages from AU, CH, MX, QZ, US and ZA.*

NCGR-Corvallis Rubus Catalog 2009, retrieved on Mar. 20, 2017, retrieved from the Internet at <http://www.ars-grin.gov/cor/catalogs/rubtc.html> 14 pp.*

* cited by examiner

*Primary Examiner* — June Hwu
(74) *Attorney, Agent, or Firm* — Rosenberg, Klein & Lee

(57) ABSTRACT

The present invention is a new and distinct floricane fruiting red raspberry cultivar named 'Pearl', which is capable of producing large quantities of commercial size and quality fruit in subtropical or warm temperate areas which experience little winter chilling. The cultivar is characterized by high bud break and vigorous flower truss growth from floricanes on low chilled plants which bear fruit early in the season. 'Pearl' fruit is light colored, truncated conic, firm, easily seen and picked and uniform; making it suitable for commercial shipping. The plant has a tendency toward trifoliolate (vs. pentafoliolate) leaves, dark red, somewhat innocuous thorns, and relatively smooth and simple leaf margins.

6 Drawing Sheets

Figure 1:
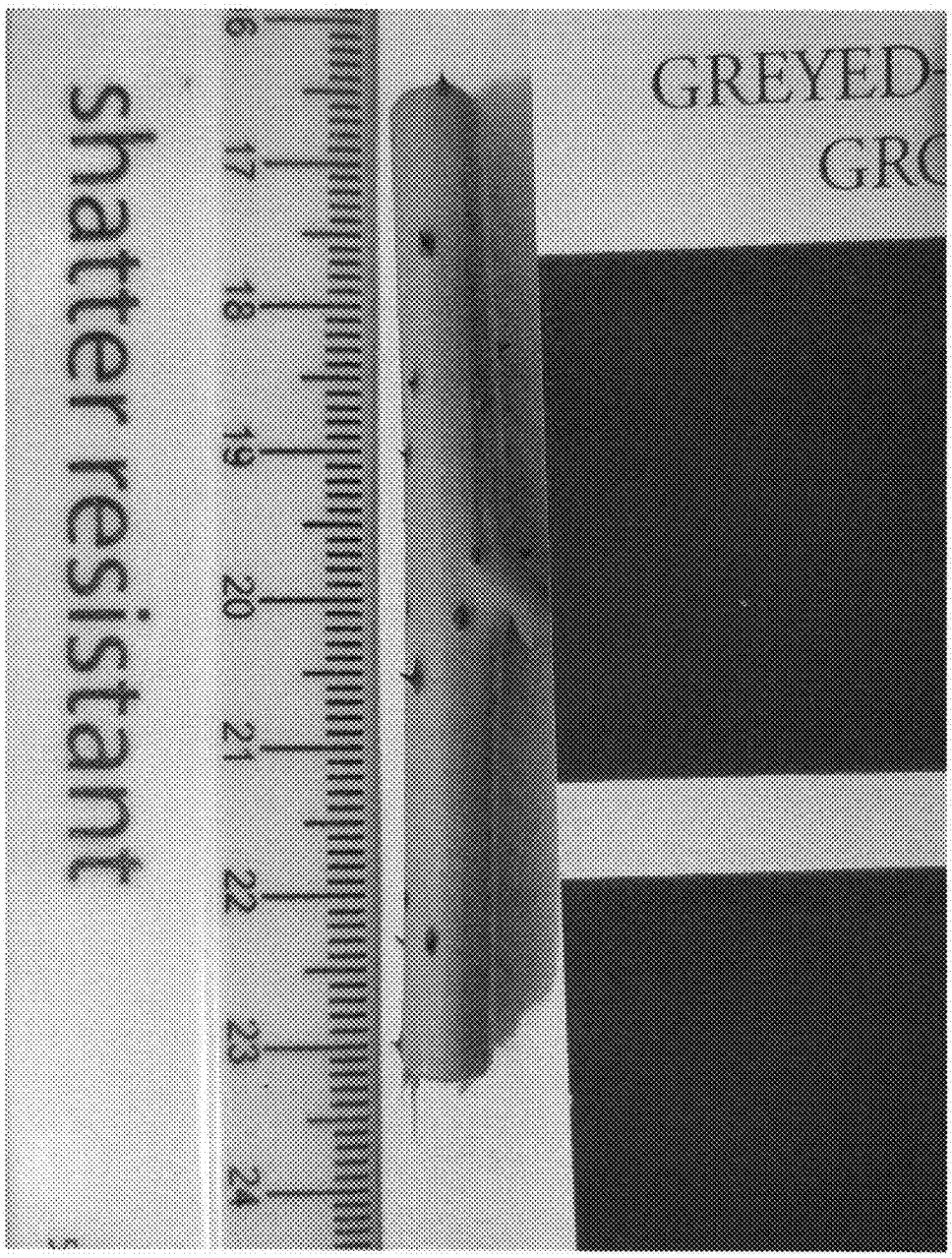

Latin name: *Rubus idaeus*. L.
Varietal denomination: 'Pearl'.

PRIORITY CLAIM

This invention claims priority under 35 U.S.C. §119(f) of application number 2014/2771 filed on 4 Nov. 2014 at the European Community Plant Variety Office (CPVO).

FIELD OF THE INVENTION

This invention concerns a new and distinct cultivar of floricane fruiting raspberry plant with a botanical name of *Rubus idaeus* L. The new cultivar, named 'Pearl', is distinguished from other cultivars by its combination of fruit firmness, size, flavor and attractiveness, earliness of cropping season, and plant productivity from overwintered canes which require very low winter chilling. 'Pearl', is thereby suitable for floricane production in subtropical and warm temperate commercial production areas which would normally rely on only primocane cultivars. These traits are valuable for very early cropping season production.

DESCRIPTION OF RELATED PRIOR ART

Several cultivars of floricane fruiting (commonly known as "spring bearing") raspberry plants are known which have either large sized, firm or attractive fruit. For instance, raspberry cultivars named 'Glen Ample', 'Josephine', 'Driscoll Maravilla', 'Cascade Bounty', 'Georgia', 'Adele', 'Marcianna', 'Wakefield', 'DrisRaspFour', 'Crimson Giant', and 'DrisRaspThree', have been described in U.S.

Plant Pat. Nos., 11,418; 12,173; 14,804; 18,246; 19,430; 20,773; 21,007; 21,185; 22,731; 23,375 and 23,477, respectively. The new and distinct cultivar of the present invention is a raspberry plant named 'Pearl', This cultivar differs from 'Josephine', 'Driscoll Maravilla', 'Marcianna', 'DrisRasp-Four', 'Crimson Giant' and 'DrisRaspThree' in bearing a large majority of its fruit only in the spring while the other cultivars can also produce large quantities of fruit on their primocanes in the late summer and fall. 'Pearl', canes are thorny, distinguishing it from 'Glen Ample' and 'Georgia' which are thornless, and 'Adele' which is minimally thorny and has spines which are smaller and lighter colored then 'Pearl'. 'Driscoll Maravilla' has larger spines than 'Pearl', and the spines on 'Pearl', are darker in color, and the color is more uniform 'Pearl', fruit is bright red in color when ripe, while other floricane-crop only cultivars 'Wakefield' and 'Crimson Giant' are dark red when ripe, resembling over ripe 'Pearl', fruit. 'Cascade Bounty' is a floricane variety with similar thorn coloration and size, however, 'Pearl', thorns are more numerous (approximately double at the base of the plant) and 'Pearl', fruit is larger, firmer and more conic than the medium sized and round 'Cascade Bounty'. For all floricane production only varieties sited above, 'Pearl', floricanes have lower overwinter chilling requirements, which result in bud break throughout the overwintered plant after minimal chilling. With insufficient chilling, high chill requiring plants only have bud break on a small number of nodes at the apex of the floricane, or if severely lacking chilling, no buds will break or there will be only a few shoots or trusses from the very base of the cane.

ORIGIN OF THE NEW CULTIVAR

The new cultivar of spring bearing, floricane, red raspberry originated from a controlled cross in Oakland, Md. The cross, designated: "KX" was ZGN-e1 (female cultivar, unpatented)×XN-1vf (male cultivar, unpatented) and was made in February and March of 2009, when there was no pollinator activity.

ZGN-e1 is a dark fruited, primocane and floricane fruiting, red raspberry selection made in Cartaya, Spain with several desirable fruit quality attributes, including fruit size and reasonable fruit firmness. Compared to ZGN-e1, 'Pearl' is primarily a floricane fruiter with lighter colored, firmer fruit and a low chilling requirement. ZGN-1ef is a cross of VDA-o2 (female selection, unpatented)×'Tulameen' (male cultivar, unpatented). VDA-o2 is a thorny dark fruited spring and fall fruiting red raspberry species hybrid with very firm and sweet fruit and very erect canes. VDA-o2 is a cross of SDO-1 (female selection, unpatented)×RH-5 (male selection, unpatented). SDO-1 is a soft fruited, but productive cross of ON-1 (female selection, unpatented)×'Emily' (U.S. Plant Pat. No. 12,350). ON-1 is a cross of HBK-5 (female selection, unpatented)×LA-2 (male selection, unpatented). HBK-5 is cross of Lauren (female cultivar, U.S. Plant Pat. No. 10,610)×NY 817 (male selection, unpatented). LA-2 is a cross of *R. inominatus* (female, wild species, unpatented)× Glen Garry (male cultivar, unpatented). RH-5 is a very vigorous cross of GEL-114 (female cultivar, unpatented)× NE-2 (male selection, unpatented). GEL-114 is a cross of 'Southland' (female cultivar, unpatented) by SCRI 86B16 (male selection, unpatented). NE-2 is a cross of FD-2 (female selection, unpatented)×Emily (male cultivar, U.S. Plant Pat. No. 12,350). FD-2 is a cross of *R. flos-culosis* (female wild species, unpatented)×'Citadel' (male cultivar, unpatented)

'XN-1vf' was selected as very early flowering (February) in Faversham, Kent, United Kingdom. XN-1vf fruit is small, rough shaped and relatively soft, which distinguishes it from the firm, large and uniform fruit of 'Pearl'. XN-1vf was a cross of Caroline (female cultivar, U.S. Plant Pat. No. 10,412)×Georgia (male cultivar, U.S. Plant Pat. No. 19,430).

This year of crossing was designated "D" as part of a virus indexed certified seed breeding program. The seed from the cross "KX" was exported to the United Kingdom, germinated and grown to one foot height in Faversham, Kent United Kingdom. The potted plants were then transported to Cartaya, Spain (the "e" location) and grown in tunnels in the soil for evaluation. The present invention was second seedling of the KX progeny selected from the floricane ("f") seedling field in March 2011 and was thereafter designated "-12ef". The field in Cartaya, Spain normally receives 250 hours of chilling (<45° F.) and temperatures over 100° F. in summer. Thus, the complete breeding designation of 'Pearl', is "DKX-12ef". Plant variety protection has been filed In the EU.

SUMMARY OF THE NEW CULTIVAR

This application relates to a new and distinct red fruited, floricane fruiting, raspberry cultivar, botanically known as *Rubus idaeus* L. The following characteristics are outstanding:

1. Production of floricane fruit which has a rare combination of commercial size, firmness, flavor, light color, attractiveness and ability to ship and store.
2. Plants of 'Pearl' require only 250 hours of chilling to flower from floricanes and the fruit production season is thereby much earlier than other cultivars when protected from frosts. This allows large quantities of winter flowering for late winter and early spring commercial production of fruit in sites considered too warm during the winter.

These characteristics make 'Pearl' suitable as a very early season floricane fruiting type for premium fresh fruit marketing in commercial low chill production areas worldwide. As 'Pearl' floricanes require only 250 hours of winter chilling for good bud break, 'Pearl' should be trusted to produce a crop in certain areas of Mexico, the southern US or south of Watsonville, Calif. Floricane fruit production has not been tested in areas that experience severe subfreezing temperatures, therefore, no claims are made concerning cold hardiness below −12° C. (10° F.).

The following characteristics are useful in distinguishing this cultivar from other cultivars and can be useful for cultivar identification. Plants used for these observations were grown in unshaded and uncrowded conditions in glasshouses, tunnels and outdoors.

1. 'Pearl' plants do not produce a considerable fall or primocane crop, even when given 160 days of good growing conditions. A majority, >80%, of primocanes do not flower in the fall. The growth of new primocanes is the only vegetative bud burst. New primocane growth occurs sporadically in the winter from cane bases and roots (with no "bud break").
2. Floricanes require less than 500 hours of exposure to temperatures between 32° and 50° F. to have adequate bud break for a full late winter or spring crop. Bud break on 'Pearl' floricanes given 250 hours of chilling occurs on all sections of the cane at percentages sufficient to produce fruit from ground level to the apical pruning cut or cane terminus; generally with an unbroken canopy. No data is available for floricane bud burst as flowering date is a more accurate determination of functional bud burst. Buds can break on high chilling types, but they fail to develop into trusses or develop into rosettes unless a sufficient amount of chilling has occurred. For 'Pearl', high rates of bud break and complete flower truss development occurs throughout the winter, indicative of a short chill requirement phenotype.

3. The initial or primary fruit is short conic; on average, the primary fruit is 20% longer than wide. Round type fruit, for example: 'Josephine', 'Cascade Bounty' and 'Driscoll Maravilla', have primary fruit with a ratio of width to length within 10% of 1 to 1. Fruit size of primary fruits grown in Maryland, United States was 2.85 cm in length and 2.28 cm in width, with an average season long fruit weight of 5.1 grams.
4. Fruit color is lighter than average, 2001 Royal Horticultural Society Colour Plate No. 47A when ripe. Fruit is easily removed from its receptacle and easily visible on medium length laterals. Fruit firmness or texture is firmer, or as firm, as the cultivars used for long distance shipping, especially after 7 days of commercial storage. Thus, in combination with its fruit size and weight, 'Pearl' is unusual for most raspberry genotypes, with the combination of fruit quality traits which allow commercial production and shipping from non-traditional production areas.
5. The coloration of the thorns on primocanes is typical of 'Pearl' in different locations and, although this coloration is found in other cultivars, thorn color can be used to distinguish 'Pearl' from some other cultivars. Primocane thorn coloration during the growing season is consistently deep grayed purple (2001 Royal Horticultural Society Colour Plate No. 183A) and the coloration extends about 1 mm. in an oval into the surrounding cane. Thorn color deepens to 2001 Royal Horticultural Society Colour Plate No. 187A in the fall and in well lighted areas of the canes. Thorns are generally 2 mm. in length, relatively thin and slightly downward pointed. Thorns on apical areas or petioles are sufficiently small to produce a bumpy sensation when rubbed, as compared to a sting from thorn penetration of the skin on longer thorn varieties.
6. Leaf margin serration is relatively uniform compared to other cultivars and leaf lobing caused by incomplete separation of leaflets, is less common than most varieties. This gives the appearance of a smooth leaf edge.

BRIEF DESCRIPTION OF THE PHOTOGRAPHS

The accompanying photographs show typical characteristics of the new variety:

FIG. 1. shows a mid-section of a 'Pearl' primocane from a 2 year old plant with 2001 Royal Horticultural Society Colour Plate No. 183 for thorn color and a cm ruler with mm gradations.

Figure 2:
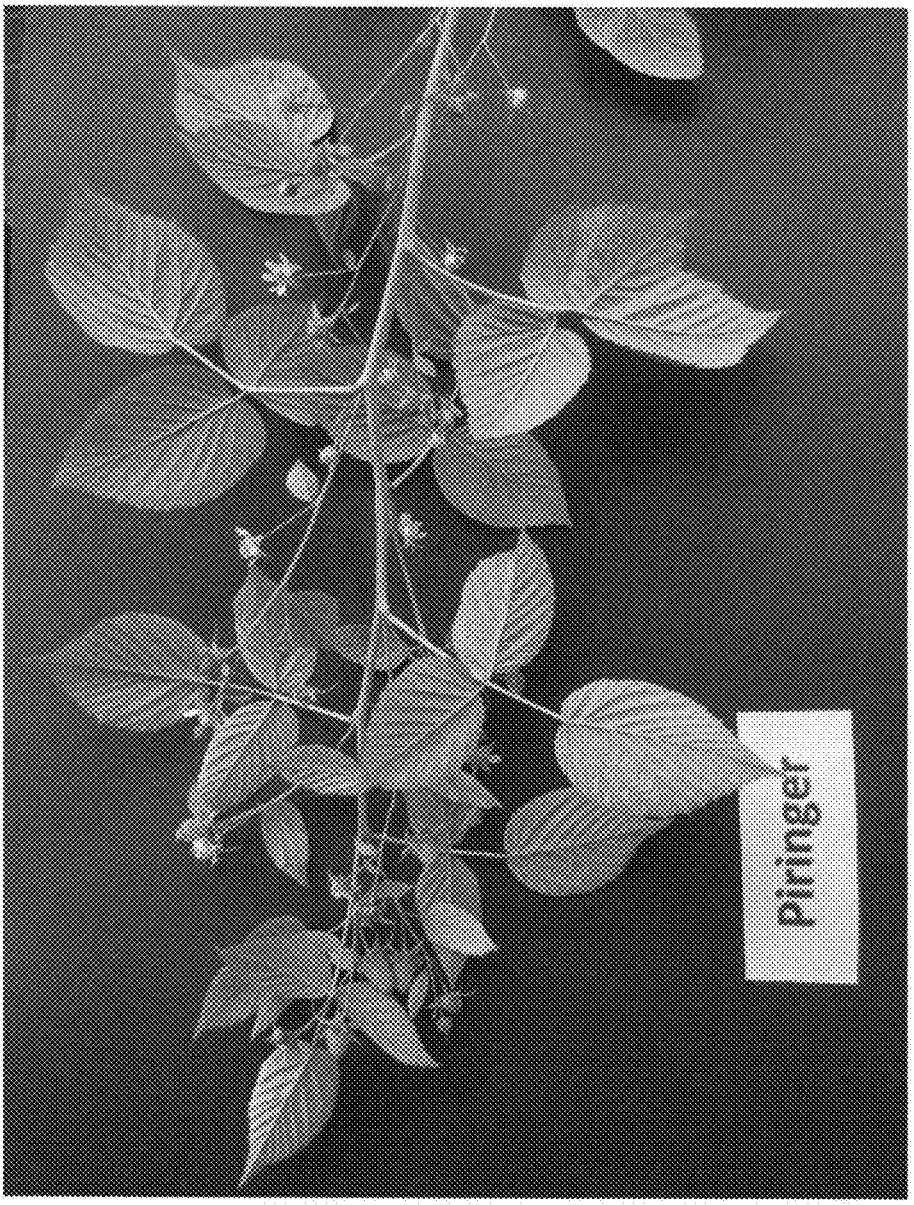

FIG. 2. shows a 'Pearl' (also known as Pringer) floricane truss from a 2 year old plant with young developing fruit and flowers and the underside of floricane trifoliolate and monofoliolate leaves.

Figure 3:
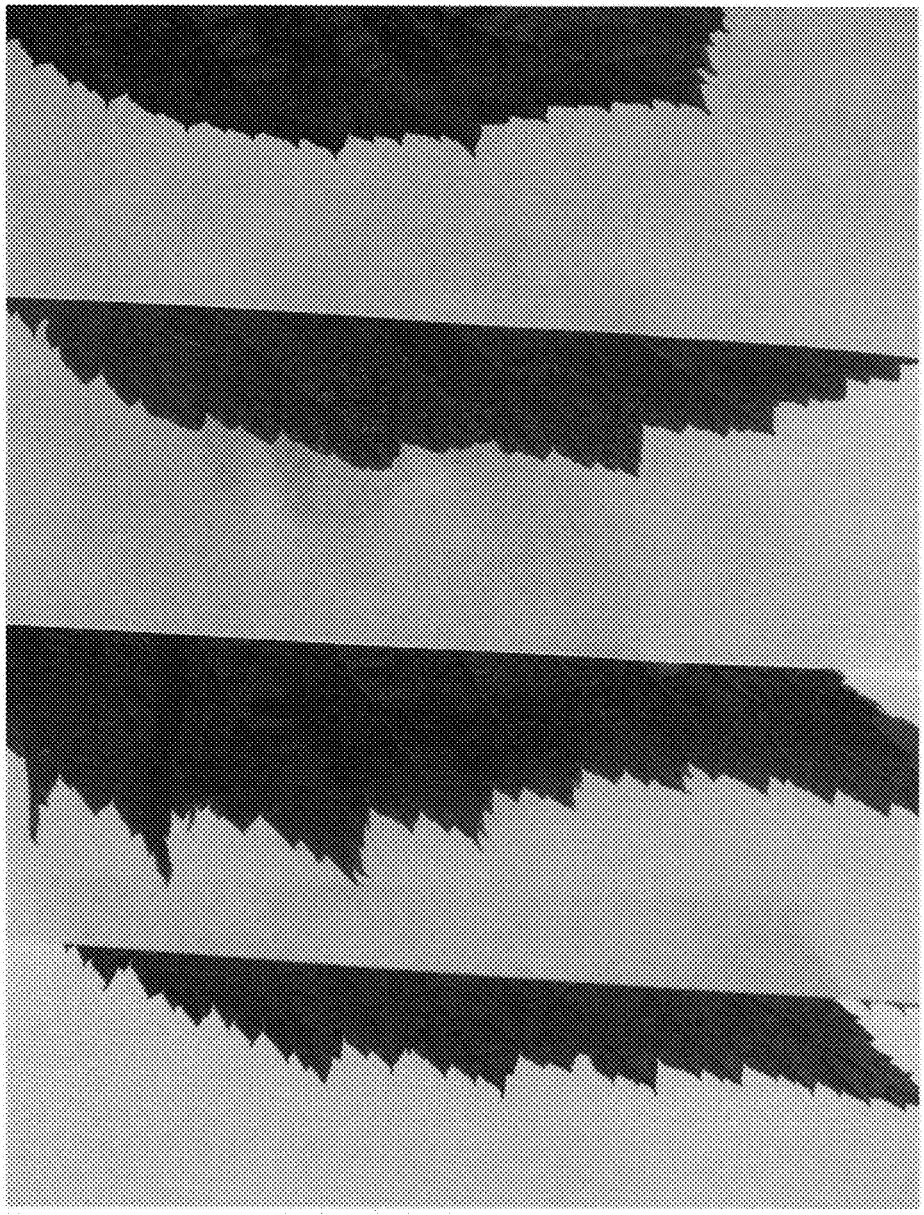

FIG. 3. shows the leaf margins of 'Marcianna', 'Anne', 'Josephine' and 'Pearl' primocane leaves from a 2 year old plant in mid-July from left to right respectively.

Figure 4:
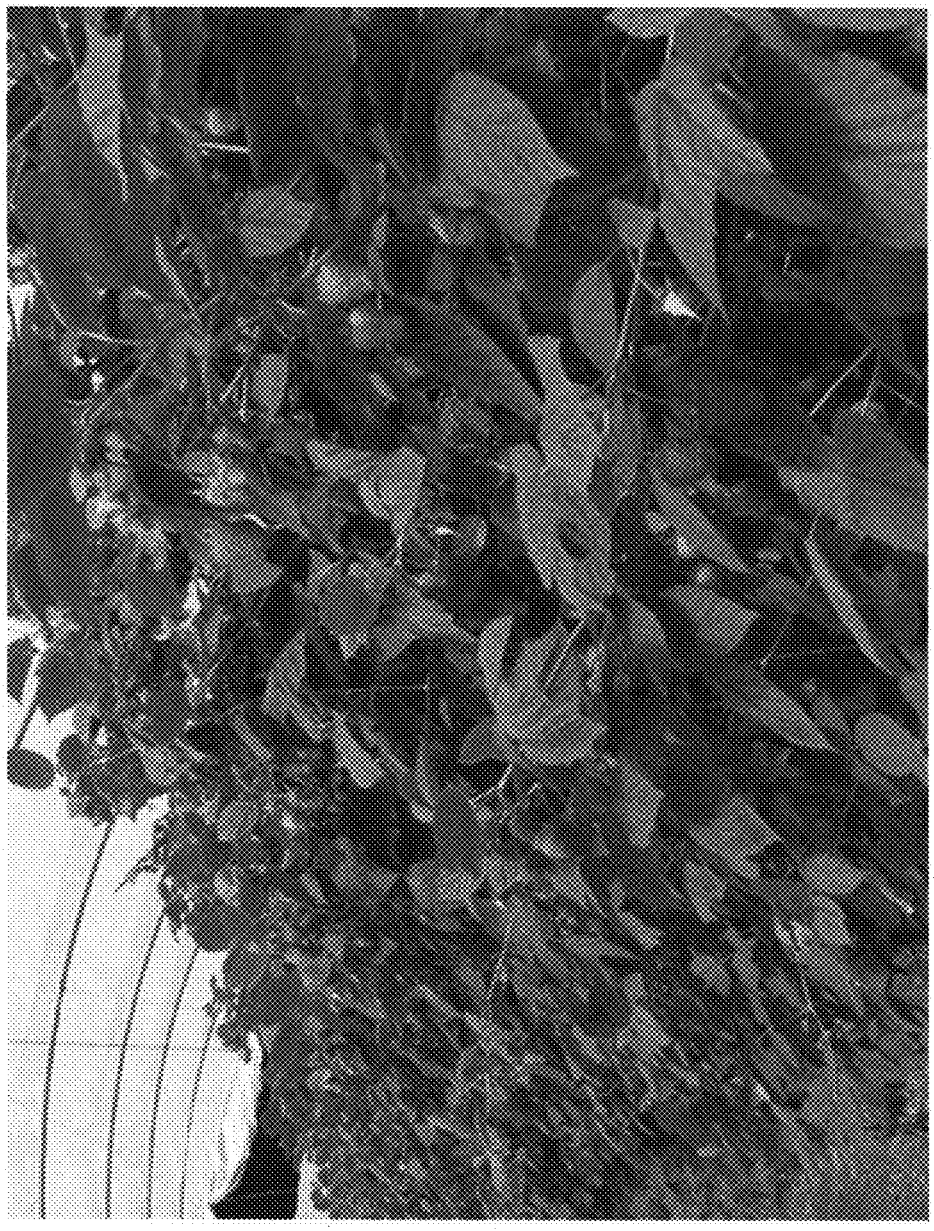

FIG. 4. shows a recently planted mid-season 'Pearl' long cane trial plot in a tunnel in Cartaya, Spain in mid-April.

Figure 5:
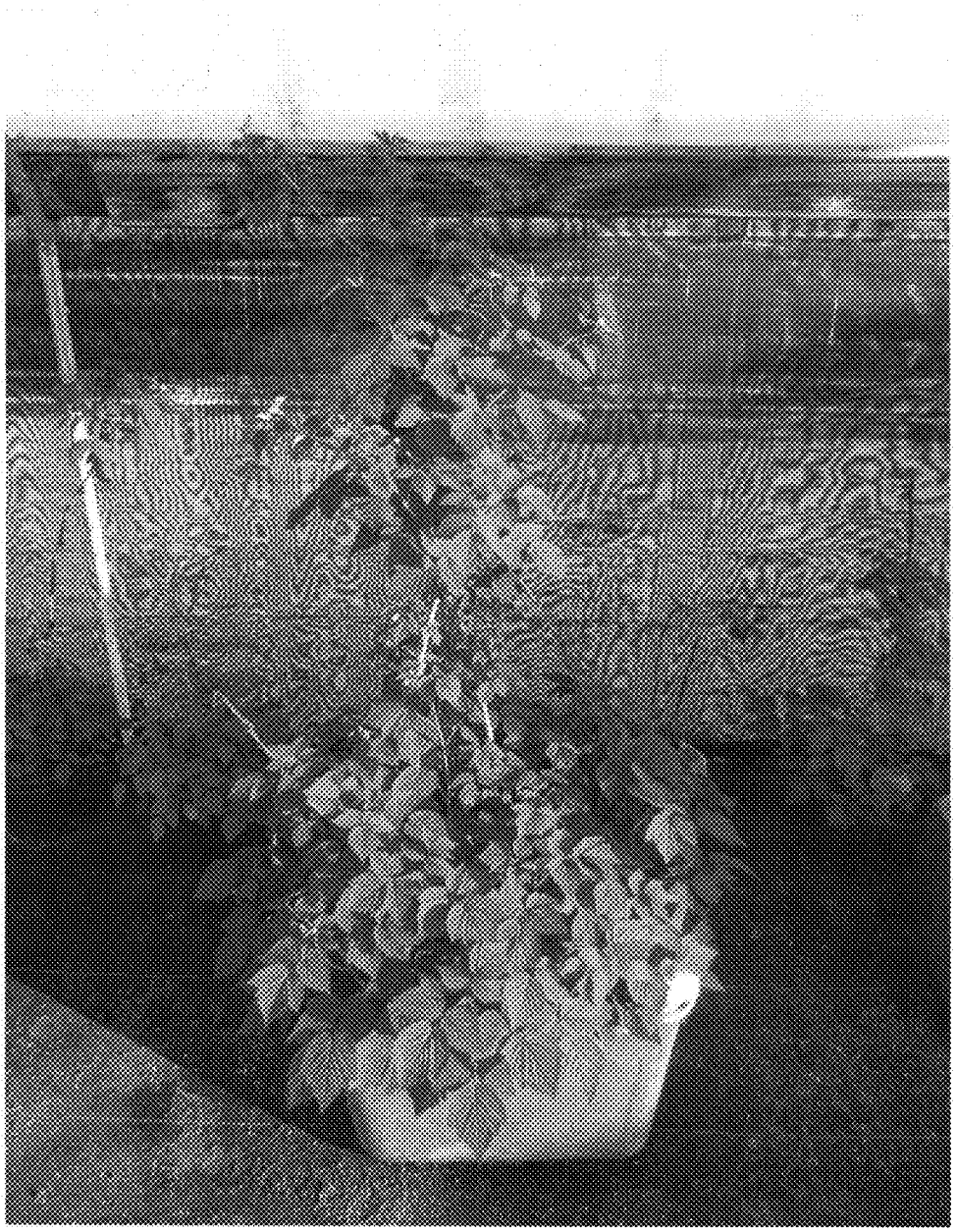

FIG. 5. shows a 2 year old 'Pearl' plant in bloom on Jan. 27, 2015 in a shade tunnel Watsonville, Calif. This plant (middle foreground), and the 'Tulameen' (far left) and 'Octavia' (immediate left) plants in the background were given 500 hours of chilling.

Figure 6:
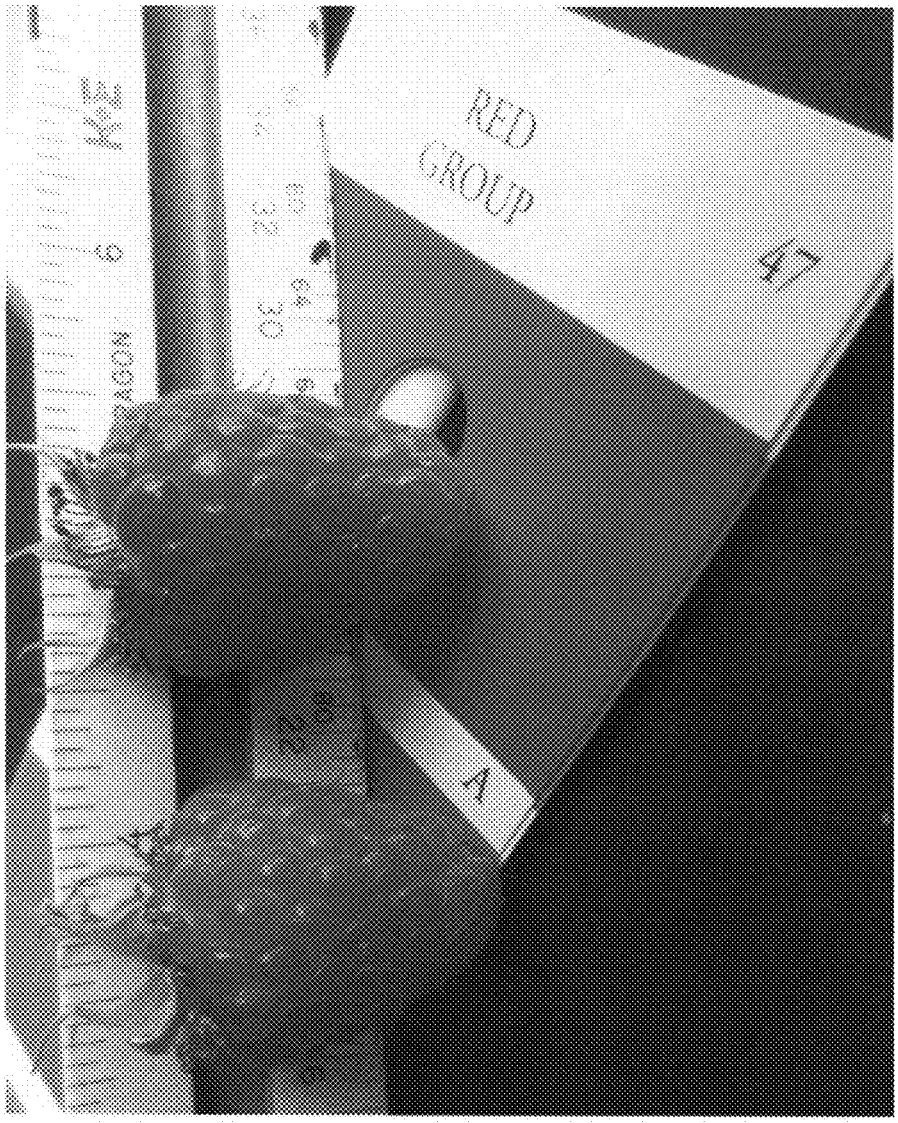

FIG. 6. shows two early season fruit of 'Pearl' from a 2 year old plant and a cm measuring stick with 1/16 inch gradations (top) and 2001 Royal Horticultural Society Colour Plate No.47A.

DESCRIPTION OF THE NEW CULTIVAR

The following is a detailed description of 'Pearl', the new cultivar, including fruit production, together with the cultivar's morphological characteristics. 'Pearl' is a *Rubus idaeus* hybrid and would be botanically classified in that species commonly referred to as red raspberries. The two Asiatic species in its ancestry may have contributed to its short chilling and some morphological characteristics, however, the general appearance of 'Pearl' is that of commercial red raspberry cultivars. The characteristics of the cultivar were compared with other standards used in the United Kingdom, Spain and Mid-Atlantic Region of the U.S. The description is based on information provided by cooperating growers from plants grown in fields at Faversham, Kent, United Kingdom and Cartaya, Spain, and from potted plants grown in greenhouses in Oakland, Md. and Watsonville, Calif., United States. As these climates differ, particularly in temperatures experienced in the growing season, we believe the description of 'Pearl' will be consistent in other locations.

In the winter and spring, 'Pearl' produces a moderate number of root- and crown-suckers (39.5 per 10 gallon pot on one-year old tissue culture plants), more than 'Anne' and 'Josephine', and similar to, 'Georgia' and 'Glen Ample', two prolific suckering floricane fruiting cultivars. These new primocanes arise in similar numbers in December or February-forced plants given 1500 more chilling hours. During the growing season, canes are light green colored (2001 Royal Horticultural Society Colour Plate No.145A) (FIG. 1) with no or a very slight amount of red blush (2001 Royal Horticultural Society Colour Plate No. 184B) in the greenhouse, but moderately blushed (30% of the surface area approximately) in full sun outdoors during the early summer.

Tissue culture produced first year plants can produce typically 0 to 8 vegetative branches if the plants are given full light and cane growth exceeds 3 meters. 'Pearl' plants are semi-erect by the second year of a plant's growth, similar to that of 'Tulameen', a grandparent. When given over 200 days of frost free conditions, growth of first year plants is very vigorous, reaching on average 161.3 inches or over 80 nodes in uncrowded conditions in tunnels. Internode length at 30 cm. above ground in well lighted plants is 4.9 cm. Cane diameter at the same position was 0.6 to 1.0 cm, including all canes. Earlier forming canes were 1.0 cm in diameter on average. Canes have a moderate and noticeable waxiness, a finger rub leaves a visible mark due to removal of the wax or "bloom". In winter, December or later, 'Pearl' floricanes are light and moderately dark brown in color, resembling in hue 2001 Royal Horticultural Society Colour Plate Nos. 177C and 177D for the medium and light brown patches respectively. In a greenhouse during the fall, this woody color onset can be later than other cultivars, such as 'Georgia' and 'Tulameen'. Floricanes exfoliate to a slight amount, less than 10% in early winter.

On canes, thorns are only moderately abundant in density: ranging from 14 to 24 per internode with an average of 20.8 at 10 nodes from the apex in mid-September to 16 to 80 per node, with an average of 50.0 at 30 cm above ground. Thorn shape is straight, slightly downward pointing, and short needle-like, with width approximately 0.5 mm in diameter at half height and length approximately 2 mm (FIG. 1). Shorter thorns occur throughout the plant, especially on petioles and peducles, but coloration is consistent. 'Pearl' thorn color is grayed purple (2001 Royal Horticultural Society Colour Plate No. 183A) in color throughout the spine; extending 1 mm. into the surrounding epidermis of the cane. This thorn coloration of the cane is in an oval oriented with the long axis parallel to the axis of the cane and blends to 2001 Royal Horticultural Society Colour Plate No.185C at the margins. Taken together, the color and amount of thorn coloring extending onto the cane is not uncommon in some red raspberries although the amount of the extension of the color is somewhat greater on 'Pearl' plants, especially considering the low to average amount of cane coloration that occurs as a blush. The color of the thorns turns darker red in the fall or earlier in full sunlight in the apical part of the cane (2001 Royal Horticultural Society Colour Plate No. 187A) then brown in the dormant season (2001 Royal Horticultural Society Colour Plate No.177D), matching that of the overwintering floricanes. A similar pattern occurs with lateral buds, which are typical in size and shape of the species, bud color in the winter is dark brown (2001 Royal Horticultural Society Colour Plate No. 177A). On occasion, 'Pearl' canes do produce secondary buds which subtend the primary bud. On average, secondary buds produce 55% of the flowers of primary buds.

Typical of the species, 'Pearl' leaf color and compoundedness are somewhat variable, being responsive to growing conditions, position on the plant, fertilization and vigor of the plant. In young plants, the lower surface of 'Pearl' leaves is pubescent grey-green resembling 2001 Royal Horticultural Society Colour Plate No.191C on primocanes and 194A and 194B on floricanes. The upper surfaces of primocane leaves are dark green, most closely in hue to 2001 Royal Horticultural Society Colour Plate No.137A in the greenhouse and outdoors and on floricane and primocane leaves. Stipule, petiole and petiolule colors are the same as that of the primocane during the growing season, 2001 Royal Horticultural Society Colour Plate No.145A and 145B, with occasional blush of similar to 2001 Royal Horticultural Society Colour Plate No.184D. Senescing leaves have a green yellow color resembling 2001 Royal Horticultural Society Colour Plate No. 146A.

In protected culture 'Pearl' primocanes on young plants have mostly trifoliolate leaves with less than 5% pentafoliolate through the growing season. More vigorous or older plants have more pentafoliolate leaves, particularly if cane diameter is greater than 1 cm. The tendency toward trifoliolate leaves increases when short days occur and the internodes of the cane at the apex shorten in response to shorter light duration and cooler temperatures. Floricane trusses have no pentafoliolate leaves, with exclusively trifoliolate leaves along the truss axis and monofoliolate leaves at the truss apex interspersed with apical fruit or terminal fruit on the short lateral trusses (FIG. 2).

Pentafoliolate terminal leaflets average 11.4 cm in length and 8.2 cm in width. The basal lateral leaflets span 22.9 cm from the apex of the right leaflet to the apex of the left leaflet if the leaves are extended to perpendicular to the leaf axis. The lateral leaflets of pentafoliolate leaves are oriented approximately 20° toward the apex of the leaf. The lateral leaflets average 7.4 cm wide at the widest point, with, on average, 43% of the leaflet on the apical side of the leaflet midrib. Pentafoliolate leaf petioles averaged 7.8 cm in length; the basal petiolule averaged 5.57 cm in length with the apical petiolule averaging 3.40 cm in length. Basal lateral leaflets have 0.8 cm leaflet stalks; apical lateral leaflets are sessile. The trifoliolate terminal leaflet is, on average, 10.9 cm wide and 13.8 cm long on primocanes and 6.2 cm wide and 7.7 cm long on floricane trusses. Monofoliolate leaves on floricane trusses are 2.8 cm long and 1.0 cm wide on average. The trifoliolate maximum leaf width, measured from apex of the lateral leaflet to the opposite lateral leaflet apex is, on average, 21.3 cm on primocanes and 13.4 cm on floricane trusses. The width of the largest basal lateral leaflet is 6.5 cm for primocanes; and 4.6 cm on floricane trusses. The trifoliolate leaf petiole and terminal petiolule lengths averaged 7.7 cm and 5.2 cm, respectively, on primocanes and 6.1 cm and 2.9 cm on floricane trusses. Petioles have between 0 and 3, and rarely up to 11, much reduced prickles with a size up to 1 mm in height. Stipules are fused to the petiole for around 0.8 cm of their base with 0.6 cm of the bladelike free stipule extending above the fused area. Trifoliolate lateral leaflets are sessile and join at the petiole apex with the apical leaf petiolule. For floral trusses, monofoliolate leaf petioles average 0.8 cm in length.

Leaf serration is relatively simple fine sawtooth and leaf margins can be regular for longer lengths than many cultivars (FIGS. 2, 3 and 4). Lobing is rare on floricane leaves; this gives the appearance of smooth edged leaves. This trait is useful in establishing the identity 'Pearl'. 'Pearl' moderate laminar puckering and veination pattern are common for most cultivars of red raspberry and cannot be used to distinguish this cultivar.

Flowers do not normally appear on unstressed and unpruned primocanes of adult 'Pearl' plants, except after 75 nodes of growth and on less than 17% of canes. In the United Kingdom, primocane flowering occurs only above 1.8 m of primocane growth; normally 2 m long canes are used for "long cane" production for Spain and Morocco. Under normal commercial growing conditions and seasons, 'Pearl' should be not be considered as a primocane fruiting variety.

A defining trait of 'Pearl' is its short chilling requirement. While almost all floricane varieties require over 1000 hours of exposure to temperatures between 32° F. and 50° F. for lateral flower bud break and floral truss development, 'Pearl' plants have consistently broken bud and flowered given only 250 hours of chill in Spain (FIG. 4). Similarly, >70% bud break and subsequent flowering occurred after less than 500 chilling hours in Watsonville, Calif. (FIG. 5). In the greenhouse in Maryland, the bud break averaged 51.4% on main canes and 71.6% on branches from canes on December forced plants and 29.5% and 55.8% on main canes and branches, respectively, on February forced plants given approximately 1500 more chilling hours.

Once buds are broken, flowering occurs on elongated flower trusses which average 12.0 or 15.3 truss nodes and either 50.9 or 52.0 cm in length for floricanes forced in a greenhouse in late December (FIG. 2) or late February, respectively. On December forced canes, of these 12.0 truss nodes, 7.2 will have flowers which produce 15.1 fruit. On February forced canes, of the 15.3 truss nodes, 10.4 will have flowers which will produce 24.9 fruit. Secondary buds can break when the primary bud is lost or the growing conditions are appropriate. Secondary flower trusses are shorter 17.7 cm in length, with 9.7 total and 5.3 flowering nodes and on average 8.3 flowers. Midpoint truss width averaged 0.5 cm on larger trusses and 0.3 cm on secondary or shorter trusses. Trusses averaged 9.1 spines per internode. Truss, blush and floricane truss thorn color are similar to that of primocanes.

Floricane flower trusses have axillary growth which can be either: longer lateral trusses with trifoliolate leaves, shorter lateral trusses with trifoliolate or monofoliolate leaves, branched lateral trusses with reduced tri- or monofoliolate leaves and either branched or unbranched peduncles, sometimes multiple from the same bud and with or without much reduced, less than 3 cm in total length, monofoliolate leaves (FIG. 2). Thus, flower trusses are typical cymose clusters on a raceme with the apical flower on the main truss axis and the apical or "king" flower on the lateral axes flowering first. The flowering sequence, by node, progresses from the apex first, with several fruit ripening at that position, then starting at the most basal nodes then acropetally toward the apex (FIGS. 2 and 4).

Flowers occur on light green, single or branched peduncles averaging 2.1 cm in length and in color, reminiscent of 2001 Royal Horticultural Society Colour Plate No. 145B (FIG. 2). Peduncles have, on average, 4.5 thorns up to 4 mm in length. Primocane trusses, when they occur, have slightly more thorns per peduncle, 12.8. No other floral characteristics were different for primocane clusters. The unscented flower morphology and early fruit morphology is typical of most red raspberry cultivars, having five white (2001 Royal Horticultural Society Colour Plate No.155D) petals that average 0.7 cm long, 0.3 cm wide on later flowers and 0.9 cm long and 0.4 cm wide on the primary, earliest flowering, "king" flowers. Petals abscise after pollination. Mid fruiting season flowers have five 0.8 cm long and 0.3 cm wide at the base triangular grey green sepals (2001 Royal Horticultural Society Colour Plate No.194B). On average, sepals are larger, 1.4 cm long, 0.4 cm wide, on primary fruits. As typical of the species, the edges of sepals are light colored (2001 Royal Horticultural Society Colour Plate No.145B) due to excess pubescence; in 'Pearl', the lines are somewhat thinner than other cultivars such as 'Georgia'. Flowers have on average 84.3 pistils on average sized midseason fruit and a smaller number of anthers on primary or lower order flowers, 48.2; none of these traits can be used to identify 'Pearl'. At full flower, 'Pearl' anthers and pistils resemble 2001 Royal Horticultural Society Colour Plate Nos. 158B and 157A, respectively.

The initial or primary fruit are easily distinguishable by its conic shape for this variety at 12 days post pollination (FIGS. 2 and 4). Ripe larger fruit is smooth conic with a medium to large sized receptacle cavity averaging 1.08 cm diameter (FIG. 6). The initial harvest mature fruit length was 2.85 cm and width was 2.28 cm, producing an initial fruit width to length ratio of 4 to 5, this ratio is equal to 'Sapphire', another conic floricane variety, but smaller than 'Marcianna' and 'Jaclyn' two long fruited cultivars with a ratio above 5 width to 7 length 'Pearl', has relatively more conic primary fruit than 'Josephine', 'Polka' and 'Driscoll Maravilla', which have more nearly round fruit and a ratio of 1 to 1. Mid to late season 'Pearl' fruit average 1.98 cm in length and 1.95 cm in width with a receptacle cavity averaging 0.82 cm 'Pearl' fruit drupelets are medium in size.

There are no irregularities to 'Pearl' fruit shape or its underlying receptacle, a smooth and unbent cone which tapers to a rounded point. With adequate width of the cavity, 48% of the fruit width, fruit removal does not result in distention of the drupelets of 'Pearl', reducing splitting during commercial picking. However, some larger fruit have an uneven collar which can separate slightly upon picking commercially, slightly unripe. 'Pearl' fruit are cohesive, but, unlike two large-fruited fall bearing cultivars: 'Josephine' and 'Anne', it will not tear across the drupelets before individual drupelets separate from each other. Unlike 'Josephine' and 'Anne', 'Pearl' fruit is not overly dusky or pubescent.

'Pearl' fruit are glossy, bright medium red when ripe, closely resembling the hue of 2001 Royal Horticultural Society Colour Plate No. 47A (FIG. 6) and slightly lighter color when underripe, resembling 2001 Royal Horticultural Society Colour Plate Nos. 50A and 50B. When green, fruit is a light green color resembling 2001 Royal Horticultural Society Colour Plate Nos.144B and 144C. The fruit receptacle, which remains on the plant after fruit harvest, is light yellow, resembling 2001 Royal Horticultural Society Colour Plate No.10D.

In a Spanish trial, appearance, flavor and texture of 'Pearl' fruit stored in a commercial refrigerator was rated higher than 'Driscoll Maravilla' after 7 days. 'Driscoll Maravilla' was rated higher if the fruit was stored at ambient room temperature, however. Firmness of 'Pearl' was considered equal to 'Driscoll Maravilla' at the start of commercial storage and greater after 4 days. At the initiation of storage, 'Driscoll Maravilla' flavor is considered superior, however, 'Pearl' fruit have preferred flavor after 7 days of storage. Therefore, for the purposes of long term shipment, 'Pearl' firmness can be classified as excellent when harvested slightly unripe and very firm when harvested at full ripeness. For firmness, appearance and flavor, 'Pearl' fruit was always rated above 'Glen Lyon', a standard cultivar used for long cane production in Spain and Morocco, In healthy plantings of 'Pearl' in the United Kingdom, class 2 or waste fruit was 8.7% of total sound fruit, mostly early fruit when pollination conditions were difficult.

FRUIT PRODUCTION AND PHENOLOGY

'Pearl' has been tested in ground trials in Kent, United Kingdom, in ground and pot trials of long canes in Cartaya, Spain and in pot culture in greenhouses in Oakland, Md., United States. In the United States trial with 2 6-ft tall canes after pruning, total yields in grams per plant was 1031.5 grams. Fruit weight (yield in weight/number of fruit harvested) was 5.05 grams; individual harvests ranged from 3.2 to 7.2 grams. In Spain, total yield in grams per plant ranged between 1078 to 1240 grams; in either pot or soil culture. In the United Kingdom, yield was 1498 grams per plant or 828 grams per cane.

In Maryland, 'Pearl' plants were forced, or placed in an artificially heated greenhouse after storage at 35° F. (2° C.) since Oct. 10, 2014. For December 26$^{th}$ forced plants, first flowering occurred on Mar. 10, 2015 (74 days) and the first fruit was ripe April 17$^{th}$, (38 days). For Feb. 3, 2015 forced plants, first flowering occurred on April 10$^{th}$ (66 days) and the first fruit was ripe May 17$^{th}$ (37 days). Yield per cane was 47% greater for February forced plants due entirely to greater number of flowers per truss on February forced plants. The greenhouse was heated to 45° F. at night, and the daytime temperatures were allowed to rise to 72° F. before ventilation. In Spain, the 5%, 50% and 95% ripeness dates were March 31, April 17 and May 1, respectively. In the United Kingdom trial in outdoor tunnels, the 5%, 50% and 95% ripe dates for 'Pearl' were: June 21, June 29 and July 15, respectively. For 'Glen Ample', an early floricane producing standard for the United Kingdom, the 5%, 50% and 95% ripeness dates were: July 10, July 26 and August 7, respectively.

The plant is slightly susceptible to late season leaf rust (*Pucciniastrum americanum* also known as yellow rust). The plant's reaction to *Phytophthora fragariae* var *rubi* root rot is unknown, but plants have survived an infestation in pots in a contaminated greenhouse. 'Pearl' plants are susceptible to powdery mildew (*Sphaerotheca macularis*) when greenhouse grown, exhibiting a contorted and smaller leaf under moderate to strong disease pressure.

The ultimate cold hardiness of 'Pearl' floricanes and the perennial crown is unknown. All tests have been in areas with midwinter temperatures above −5° C. The short chilling requirement and rapid flowering of this variety would indicate that 'Pearl' floricanes would be winterkilled in areas which experience over 500 chilling hours and temperatures less than −7° C. in the spring, the temperature where green raspberry tissue is killed. Heat tolerance of 'Pearl' seems to be good as the original seedling survived temperatures over 40° C. in the summer before it was selected. No subsequent testing for high temperature hardiness, especially with a heavy crop, was attempted.

'Pearl' can be asexually propagated by tissue culture or by root suckers. The tissue culture propagation was by lateral vegetative bud. The tissue culture propagation and root sucker production was was done in laboratories in Faversham, Kent, United Kingdom and Oakland, Md., United States of America. As trueness to type is required, tissue culture propagation started with lateral (non-floral) buds to initiate cultures. Once established, the in vitro lateral buds were forced to branch with the addition of benzyl amino purine. Rooting was accomplished on divided in vitro shoots using indole butyric acid and no benzyl amino purine. In the absence of adventitious shoots, the aim was to propagate using meristems. No off-type plants have been observed in the history of asexual propagation of this cultivar by either method.

What is claimed is:

1. A new and distinct spring bearing, floricane, red raspberry plant known as 'Pearl' as described herein, illustrated and identified by the characteristics set forth above.

* * * * *